(12) United States Patent
Liu et al.

(10) Patent No.: US 9,540,559 B2
(45) Date of Patent: Jan. 10, 2017

(54) BETAINE SURFACTANTS AND PREPARATION METHODS AND USES THEREOF

(75) Inventors: Chunde Liu, Beijing (CN); Shiyi Yuan, Beijing (CN); Demin Wang, Beijing (CN); Xinmin Song, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 431 days.

(21) Appl. No.: 13/985,735

(22) PCT Filed: Mar. 11, 2011

(86) PCT No.: PCT/CN2011/000389
§ 371 (c)(1),
(2), (4) Date: Dec. 13, 2013

(87) PCT Pub. No.: WO2012/122667
PCT Pub. Date: Sep. 20, 2012

(65) Prior Publication Data
US 2014/0113842 A1    Apr. 24, 2014

(51) Int. Cl.
*C09K 8/584* (2006.01)
*C07C 309/14* (2006.01)
*C07C 229/14* (2006.01)

(52) U.S. Cl.
CPC ............. *C09K 8/584* (2013.01); *C07C 229/14* (2013.01); *C07C 309/14* (2013.01)

(58) Field of Classification Search
None
See application file for complete search history.

(56) References Cited

U.S. PATENT DOCUMENTS

| 3,326,768 A * | 6/1967 | MacMillan | A61K 8/49 424/65 |
| 4,479,894 A | 10/1984 | Chen et al. | |
| 4,554,974 A * | 11/1985 | Kalpakci | C09K 8/584 166/246 |

FOREIGN PATENT DOCUMENTS

| CN | 1566256 A | 1/2005 |
| CN | 1730149 A | 2/2009 |

OTHER PUBLICATIONS

Wen-Xiang Wu et al., "Interfacial Activity of Sulfobetaine BS11 as Surfactant for EOR," Oilfield Chemistry, Mar. 25, 2007, vol. 24 No. 1, pp. 57-59.

(Continued)

*Primary Examiner* — Jeffrey Washville
(74) *Attorney, Agent, or Firm* — Brinks Gilson & Lione

(57) ABSTRACT

Betaine surfactants of formula (I) and preparation methods and uses thereof are provided. The surfactant can decrease the interfacial surface tension of crude oil till $10^{-3}$ mN/m, have the capabilities of antiheating (130° C.), antimineralizing and antidiluting, and can be used in the field of tertiary oil recovery.

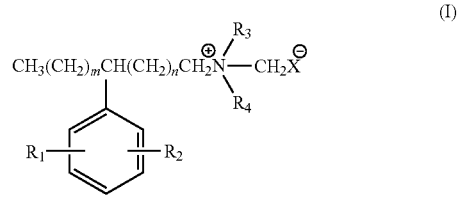

11 Claims, 7 Drawing Sheets

(56) References Cited

OTHER PUBLICATIONS

Gao Ming et al., "A New Sulphobetaine as Surfactant for EOR in Low Permeability Sandstone Reservoirs," Sep. 25, 2008, vol. 25 No. 3, pp. 265-267 and 244.
International Search Report, International Application No. PCT/CN2011/000389, Nov. 24, 2011, 8 pages.

* cited by examiner

BETAINE SURFACTANTS AND PREPARATION METHODS AND USES THEREOF

The present application is the national phase application of PCT Application No. PCT/CN2011/000389, filed Mar. 11, 2011, the entirety of which is hereby incorporated by reference.

FIELD OF THE INVENTION

The present invention relates to surfactants, in particular, to betaine surfactants and the preparation and uses thereof.

BACKGROUND OF THE INVENTION

The main oilfields in China such as Daqing oilfield, Shengli oilfield, and Liaohe oilfield etc. have entered the late stage of secondary oil recovery having high water cut and extra-high water cut. In order to improve the ultimate recovery of the existing oilfields, it is desirable to exploit tertiary oil recovery technique. Combined chemical flooding technique is a new tertiary oil recovery technique developed in 1980's, which combines alkali, surfactant and polymer and takes advantage of the synergistic effect between each agent. Such technique not only can substantially reduce the interfacial tension of oil-water and increase the microscopic oil displacement efficiency, but also can increase the viscosity of the displacing fluid so as to have relatively high swept efficiency, thereby substantially improving the recovery efficiency. In practice, due to the use of the strong alkali and the too high dosage, sonic disadvantages are observed, such as the alkali consumption and scaling, damage of formation, decrease of the viscosity of displacing fluid, and the severe oil/water emulsification, which significantly increases the difficulty in the treatment of produced liquid and cost, affects the lifting technique in oil production and causes severe facility corrosion. Therefore, alkali, especially strong alkali should be avoided in combined flooding. The systems with weak alkali or without alkali have higher viscosity and elasticity than that of strong alkali ASP flooding, which can reduce the amount of polymer and increase the sweep efficiency. Moreover, the formulation on the spot, devices for injection and processing of such systems are easier than those of ASP systems, which can reduce the cost. Therefore, it is the developing trend of the combined flooding to use weak alkali and alkali-free systems, to which the oilfield developers have paid increasing attention. However, at present, the biggest constraint for developing weak alkali/alkali-free systems is the development of high efficiency surfactants. Compared with strong alkali ASP flooding, weak alkali/alkali-free combined flooding weakens the effect of alkali, thus making it more difficult to reach ultra-low interfacial tension. Presently, the surfactants in research remain at the stage of laboratory screening with high cost, which cannot satisfy the need of practical production.

Betaine surfactants are amphoteric surfactants. Due to their chelating effect on metal ions, most of the betaine surfactants can be used for oil displacement of high salinity and high temperature reservoirs, and are capable of substantially reducing the chromatographic separation effect which occurs when nonionic surfactant is combined with anionic surfactant. The betaine surfactants mainly include carboxyl betaine type and sulfo-betaine type. The use of sulfo-betaine amphoteric surfactants in tertiary oil recovery has been reported in US patents. Such surfactants solutions prepared by high salinity water with high divalent ion content are very effective in reducing the oil-water interfacial tension, and have good emulsification and solubilization properties. Darling Petroleum College has successfully developed a new carboxyl betaine BS13 surfactant system. The results of in-lab displacing experiment show that BS13 oil-displacing system has better oil-displacing effect than strong alkali ASP system. However, the synthetic routes of such surfactant BS13 is complicated, with high cost, and the production craft needs to be improved.

SUMMARY OF THE INVENTION

The object of the present invention is to provide a betaine surfactant which is tolerant to brine and water with high salinity, and is capable of reaching ultralow interfacial tension in low concentration when used for binary combined flooding.

The betaine surfactant is represented by formula (I):

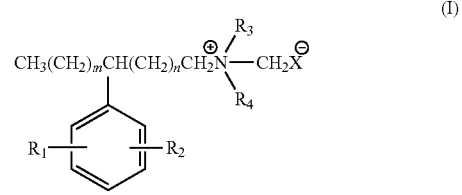

wherein at least one of m and n is a positive integer greater than 0, $R_1$ and $R_2$ are independently H or alkyl, $R_3$ and $R_4$ are independently alkyl, X is selected from the group consisting of

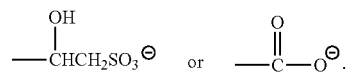

m and n are positive integers of 2-10, and m+n=5-19, $R_1$ and $R_2$ are independently H or C1-C8 alkyl, $R_3$ and $R_4$ are independently C1-C4 alkyl.

m+n is an integer of 9-17, $R_1$ and $R_2$ are independently H or C1-C4 alkyl, $R_3$ and $R_4$ are independently C1-C2 alkyl.

m and n are 7 or 8 respectively, and m+n=15, $R_1$ and $R_2$ are independently H or C1-C2 alkyl.

The specific structures of the betaine surfactant as described above are selected from the group consisting of:

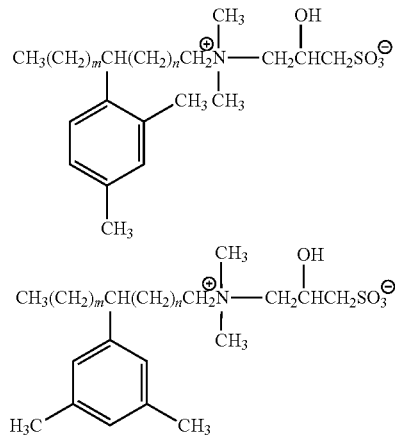

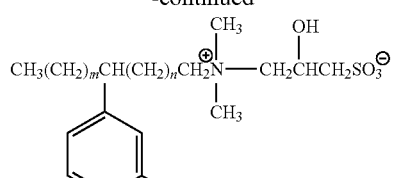
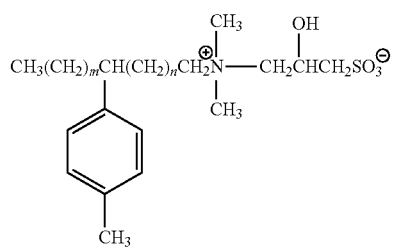
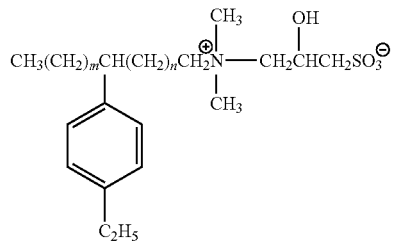
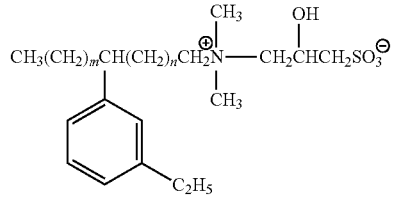
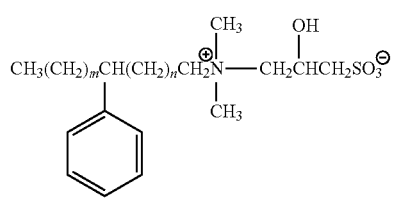
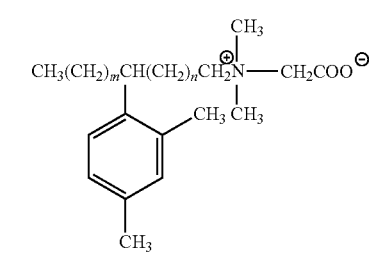
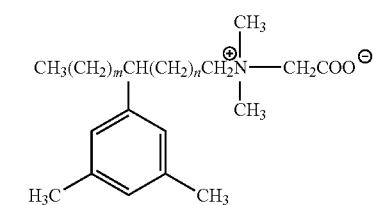
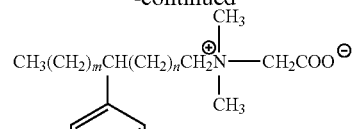
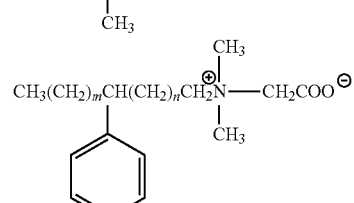
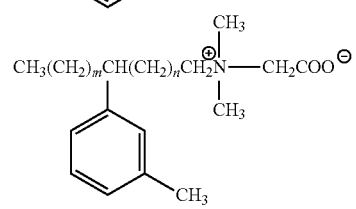
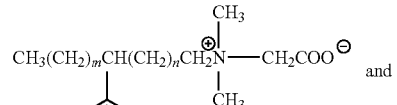
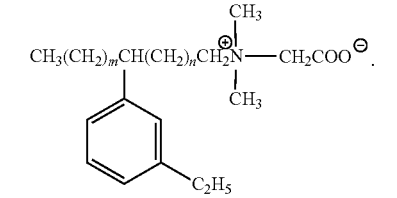
and
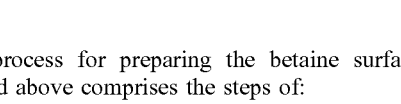

The process for preparing the betaine surfactants as described above comprises the steps of:
(1) Friedel-Crafts alkylation: Friedel-Crafts reaction between olefinic acid or olefinic acid ester and alkylbenzene or benzene catalyzed by protonic acid takes place to produce aryl alkyl carboxylic acid or aryl alkyl carboxylate;
(2) Hydrogenation reduction: the aryl alkyl carboxylic acid or aryl alkyl carboxylate is de-esterified to remove the protective groups via catalytic hydrogenation, so as to produce aryl fatty alcohol;
(3) Amination: aryl fatty tertiary amine is produced from aryl fatty alcohol and secondary amine through Cu—Ni composite catalyst;
(4) Quaternization: aryl fatty tertiary amine is reacted with sodium chlorohydroxypropyl sulfonate or sodium chloroacetate to produce the target product.

The olefinic acid is oleic acid.
The olefinic acid ester is olefinic acid methyl ester.
The alkylbenzene is selected from the group consisting of toluene, xylene and ethylbenzene.
The secondary amine is selected from the group consisting of dimethylamine and diethylamine.
The reaction condition of quaternization is: aryl fatty tertiary amine is reacted with chlorohydroxypropyl sulfonate or sodium chloroacetate in methanol solvent at 130° C. and 0.3 MPa, so as to produce the target product.

The reaction condition of amination is: aryl fatty alcohol is reacted with gaseous secondary amine at 180-250° C. and 0.3 MPa under the catalysis of Cu—Ni composite catalyst (please see patent CN1316297, CN1110629, and China Surfactant Detergent & Cosmetics, Vol. 25, issue 2, 2005), yielding aryl fatty tertiary amine.

The reaction condition of Friedel-Crafts alkylation is: react alkylbenzene or benzene with olefinic acid or olefinic acid methyl ester in an amount of 5 times of the amount of alkylbenzene or benzene in the presence of protonic acid catalyst at 115-120° C. and 0.2 MPa, yielding aryl alkyl carboxylic acid methyl ester.

The protonic acid is selected from the group consisting of methanesulfonic acid, phosphoric acid, sulfuric acid and hydrofluoric acid.

The reaction condition of hydrogenation reduction is: aryl alkyl carboxylic acid or aryl alkyl carboxylic acid methyl ester is hydrogenation reduced into aryl a octadecyl alcohol under the catalysis of CuO—ZnO—Cr$_2$O$_3$ hydrogenation catalyst at 200-350° C. and 25-30 MPa.

The betaine surfactants of the present invention are prepared by the Friedel-Crafts reaction between olefinic acid or olefinic acid ester and benzene or alkylbenzene followed by hydrogenation to produce aromatic fatty alcohol. The aromatic fatty alcohol is reacted with tertiary amine to produce aromatic fatty tertiary amine, which is further reacted with sodium chlorohydroxypropyl sulfonate or sodium chloroacetate to produce the betaine surfactants of the present invention. The alkylbenzene is selected from the group consisting of monoalkylbenzene and dialkylbenzene. The C chain of the substituted alkyl is preferably C1-C8, more preferably C1-C4, and most preferably C1-C2. The substituted alkyl in secondary amine R$_3$NR$_4$ is preferably C1-C4. Since it is better to use gaseous secondary amine in the reaction, the substituted alkyl in secondary amine R$_3$NR$_4$ is more preferably C1-C2. Most preferably, the two alkyl substituents are simultaneously C1 or C2, that is, the secondary amine is selected from the group consisting of diethylamine and dimethylamine. The structure of the olefic acid or olefic acid ester comprises C8-C22, more preferably C12-C20, most preferably the length of the C chain is 18 (m=7-8, n=7-8, m+n=15, i.e., oleic acid or oleate). Since the hydrogenation condition for aryl alkyl carboxylic acid formed by oleic acid is harsher, oleic acid is preferably esterified prior to the reaction. The hydrogenation is easier especially when oleic acid methyl ester is obtained.

The embodiments of the present invention produce octadecylsulfo betaine containing aryl groups from cheap industrial starting materials such as oleic acid and toluene or m-xylene successively subjected to esterification, Friedel-Crafts alkylation, hydrogenation reduction, amination and quaternization. The starting materials for this synthetic route are cheap, and the synthetic route is well-developed and has high yield. In addition, the product comprises aryl groups desired for tertiary oil recovery, which is because it is necessary to incorporate aryl groups into carbon chains to improve the compatibility with crude oil due to the presence of a large number of aromatic compounds in petroleum oil.

The synthetic route of the present invention is as follows:

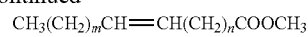

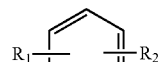

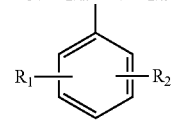

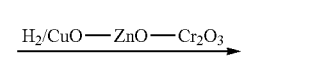

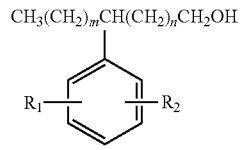

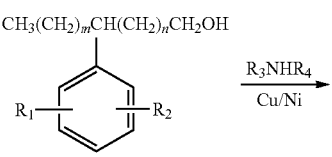

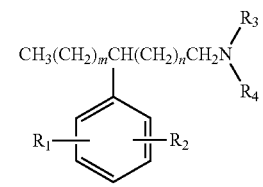

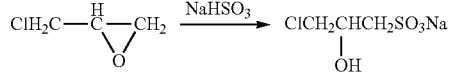

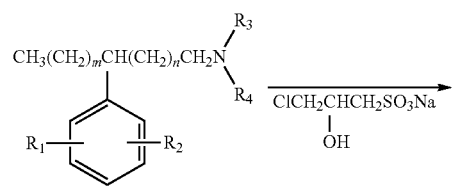

or

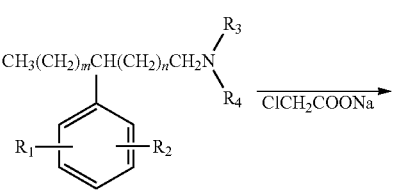

-continued

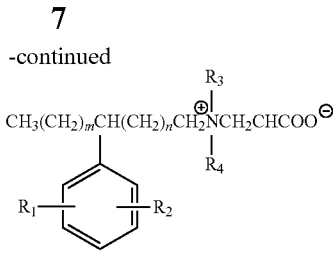

DESCRIPTION OF DRAWINGS

FIG. 6b is the attribution of the signals of the $^1$H-NMR spectrum of FIG. 6a;

FIG. 7b is the attribution of the signals of the $^1$H-NMR spectrum of FIG. 7a;

DETAILED DESCRIPTION OF THE INVENTION

Example 1

(1) Esterification: oleic acid is mixed with excess amount of methanol, and concentrated sulfuric acid or p-toluenesulfonic acid is added as catalyst. The mixture is heated to reflux for 10 h. The mixture is cooled and neutralized to pH 8-9 with sodium methoxide, washed to neutral with water, dried with anhydrous calcium chloride and distilled under reduced pressure, yielding oleic acid methyl ester;

(2) Friedel-Crafts alkylation: m-xylene (3.5 mol) and methanesulfonic acid (0.75 mol) are added into sealed reactor. The mixture is purged with nitrogen for 10 min at room temperature, and raised to 120-135° C. at 0.15 MPa. The reaction product of step (1) alkenyl carboxylic acid methyl ester (1 mol) is added dropwise, the addition time being controlled in 6 h. After the completion of the addition, the reaction is continued for 3 h. The reaction mixture is cooled to room temperature, allowed to stand for layering. Iced water having a volume equivalent to that of the methanesulfonic acid is slowly added. The mixture is rinsed 3 times, and lower layer of aqueous solution of methanesulfonic acid is separated and recovered for storage. The upper liquid is washed with iced water for 3 times, dried, and refined at 100 MPa and 220° C. to yield aryl alkyl carboxylic acid methyl ester. The conversion ratio of alkenyl carboxylic acid methyl ester is above 95% as measured by Gas chromatography-mass spectrometry with external standard;

(3) Hydrogenation reduction: the reaction product of step (2) xylene methyl oleate is hydrogenation reduced to xylene α octadecanol by hydrogenation catalyst CuO—ZnO—Cr$_2$O$_3$ at 200-350° C. and 25-30 MPa. The determination of structure is shown in FIGS. 1 and 2.

Figure 1:
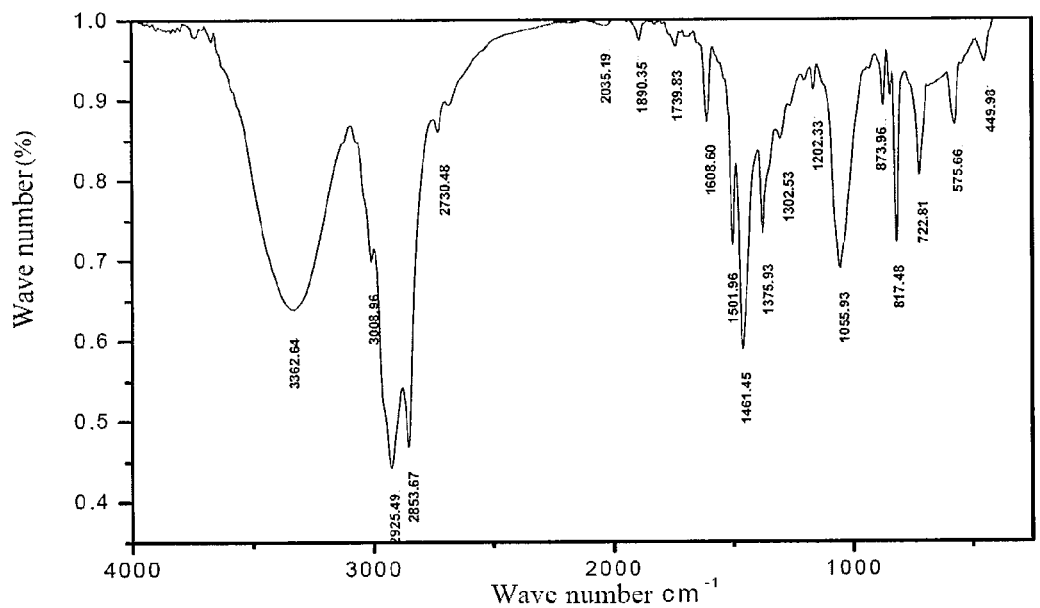
FIG. 1 is the infrared spectrum of the product of step 3 in example 1.
Figure 2:
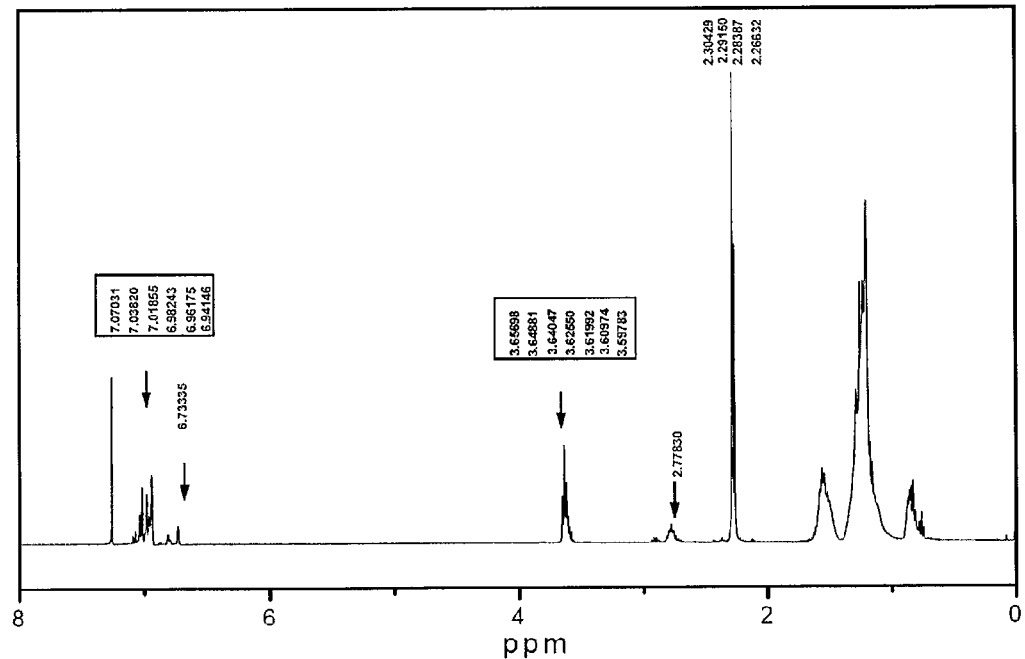
FIG. 2 is the $^1$H-NMR spectrum of the product of step 3 in example 1.

Infrared Spectrum:

As shown in FIG. 1, there is a relatively large associative O—H stretching vibration peak of alcohol at 3332.64 cm$^{-1}$. The peak at 1055.93 cm$^{-1}$ (stretching absorption of C—O bond) proves the presence of primary amine. There are peaks at 3008.96 cm$^{-1}$ (stretching vibration of Ar—H); 1608.60 cm$^{-1}$, 1501.96 cm$^{-1}$ (skeletal vibration of benzene ring); 817.48 cm$^{-1}$ (out-of-plane deformation vibration of Ar—H of meta-di-substituted benzene); 2925.49 cm$^{-1}$, 2853.67 cm$^{-1}$ (stretching vibration of saturated C—H of methyl); 1461.45 cm$^{-1}$, 1375.93 cm$^{-1}$ (bending vibration of C—H of methyl).

$^1$HNMR:

As shown in FIG. 2, from $^1$HNMR data, it is indicated that the molecular structure is substantially consistent, that is, the product obtained is substantially consistent with theoretical values.

(4) Amination: the reaction product of step (3) xylene α octadecanol is reacted via Cu/Ni composite catalyst with excess amount of gaseous dimethylamine at 180-250° C. and 0.3 MPa, yielding xylene α octadecyl tertiary amine. The spectra confirming the structure are shown in FIGS. 3 and 4.

Figure 3:
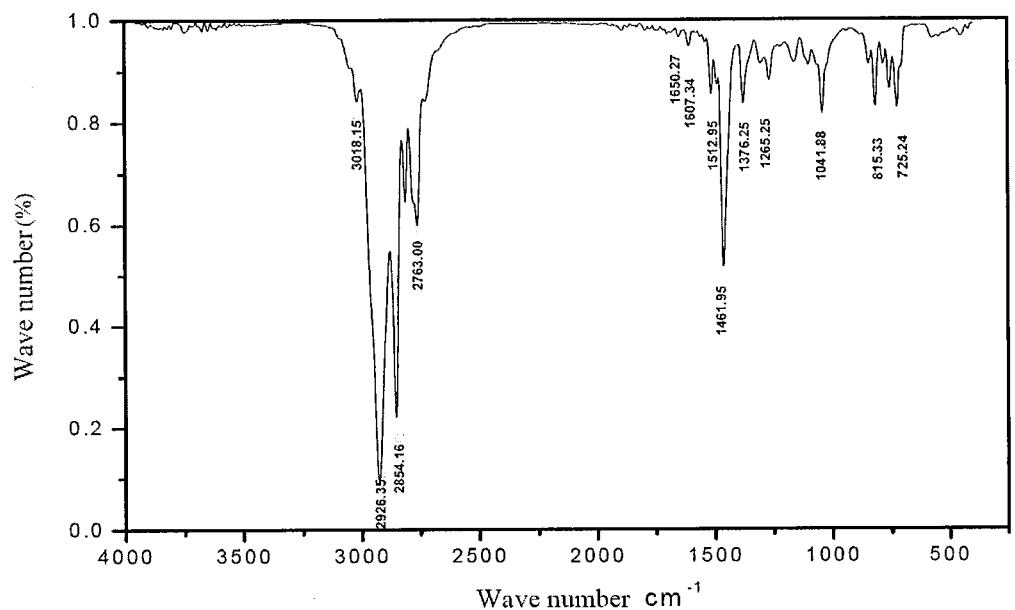
FIG. 3 is the infrared spectrum of the product of step 4 in example 1.
Figure 4:
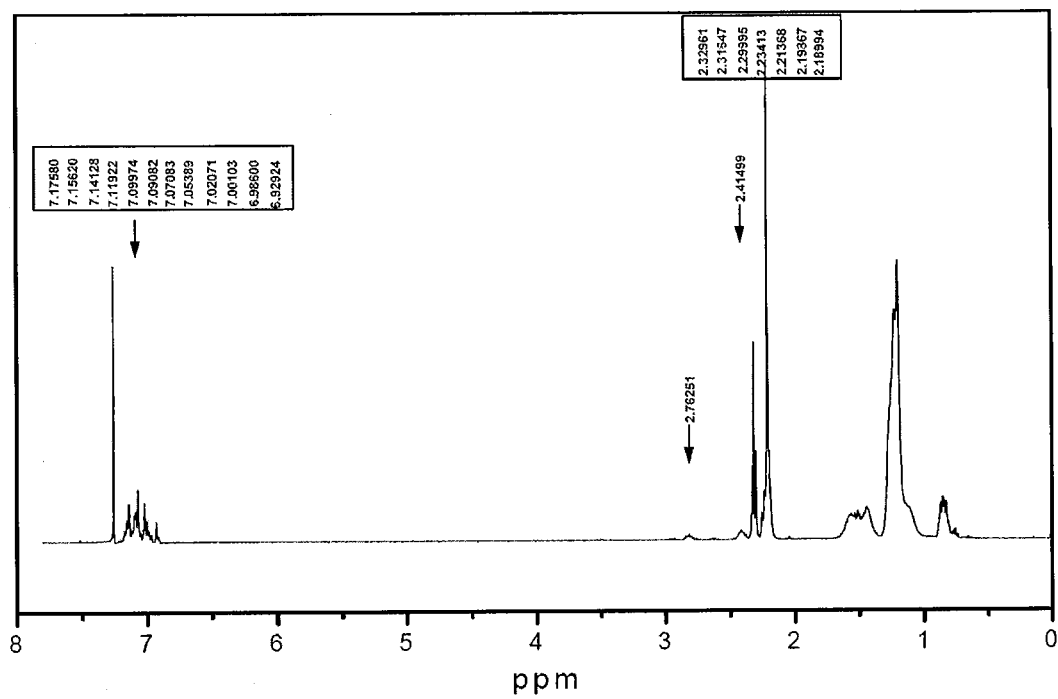
FIG. 4 is the $^1$H-NMR spectrum of the product of step 4 in example 1.

Infrared Spectrum:

As shown in FIG. 3, there are peaks at 3018.15 cm$^{-1}$ (stretching vibration of Ar—H); 1607.27 cm$^{-1}$, 1512.95 cm$^{-1}$ (skeletal vibration of benzene ring); 815.33 cm$^{-1}$ (out-of-plane deformation vibration of Ar—H of para-substituted benzene); 2926.35 cm$^{-1}$, 2854.16 cm$^{-1}$ (stretching vibration of saturated C—H of methyl); 1461.95 cm$^{-1}$, 1376.25 cm$^{-1}$ (bending vibration of C—H of methyl).

$^1$HNMR:

As shown in FIG. 4, from $^1$HNMR data, it is indicated that the molecular structure is substantially consistent, that is, the product obtained is substantially consistent with theoretical values.

(5) Quaternization: the reaction product of step (4) xylene α octadecyl tertiary amine is reacted with equivalent amount of sodium chlorohydroxypropyl sulfonate in methanol solvent at 130° C. and 0.3 MPa, yielding target betaine surfactant. The spectra confirming the structure are shown in FIGS. 5 and 6.

Figure 5:
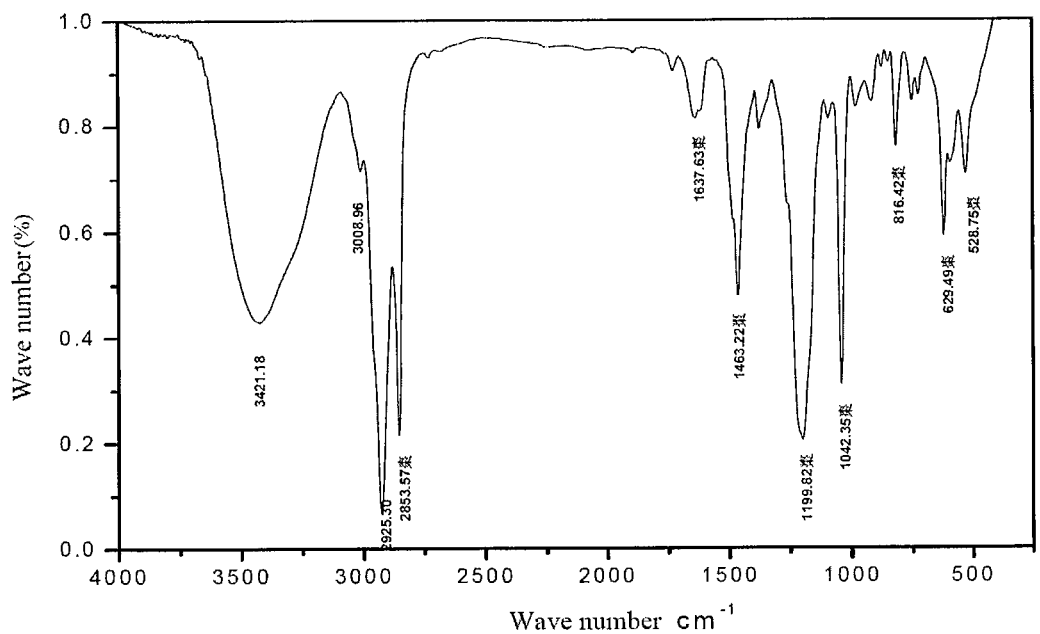
FIG. 5 is the infrared spectrum of the product of step 5 in example 1.

Infrared Spectrum:

As shown in FIG. 5, there is a relatively large associative O—H stretching vibration peak of alcohol at 3421.18 cm$^{-1}$. There are peaks at 3008.96 cm$^{-1}$ (stretching vibration of Ar—H); 1637.63 cm$^{-1}$, 1463.2 cm$^{-1}$ (skeletal vibration of benzene ring); 816.48 cm$^{-1}$ (out-of-plane deformation vibration of Ar—H of meta-substituted benzene); 2925.30 cm$^{-1}$, 2853.57 cm$^{-1}$ (stretching vibration of saturated C—H of methyl); 1199.82 cm$^{-1}$ (antisymmetric stretching vibration of —SO$_3$); around 1042.35 cm$^{-1}$ (stretching vibration of C—N of tertiary amine); 629 cm$^{-1}$ (out-of-plane bending vibration of —SO$_3$).

Figure 6A:
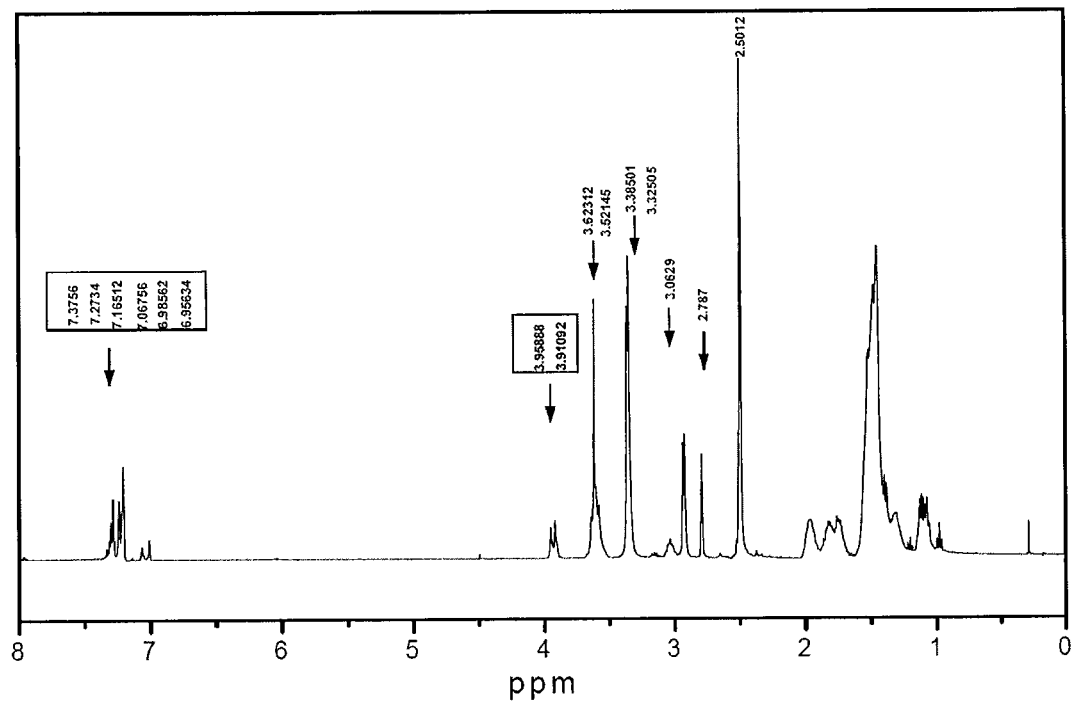
FIG. 6a is the $^1$H-NMR spectrum of the product of step 5 in example 1.
Figure 6B:
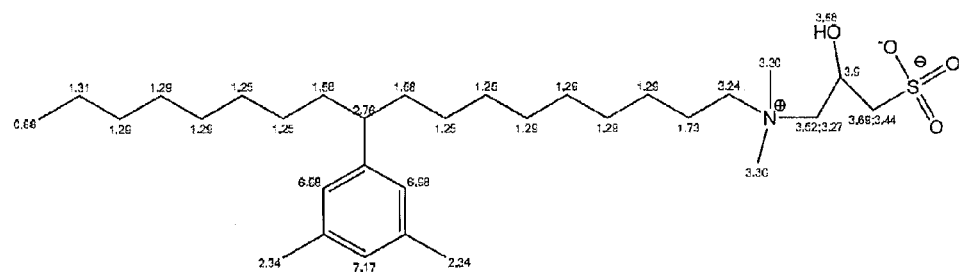

¹HNMR:

As shown in FIGS. 6a and 6b, from ¹HNMR data, it is indicated that the molecular structure is substantially consistent, that is, the product obtained is substantially consistent with theoretical values.

Example 2

Steps 1-4 are as Described in Example 1

Figure 7A:
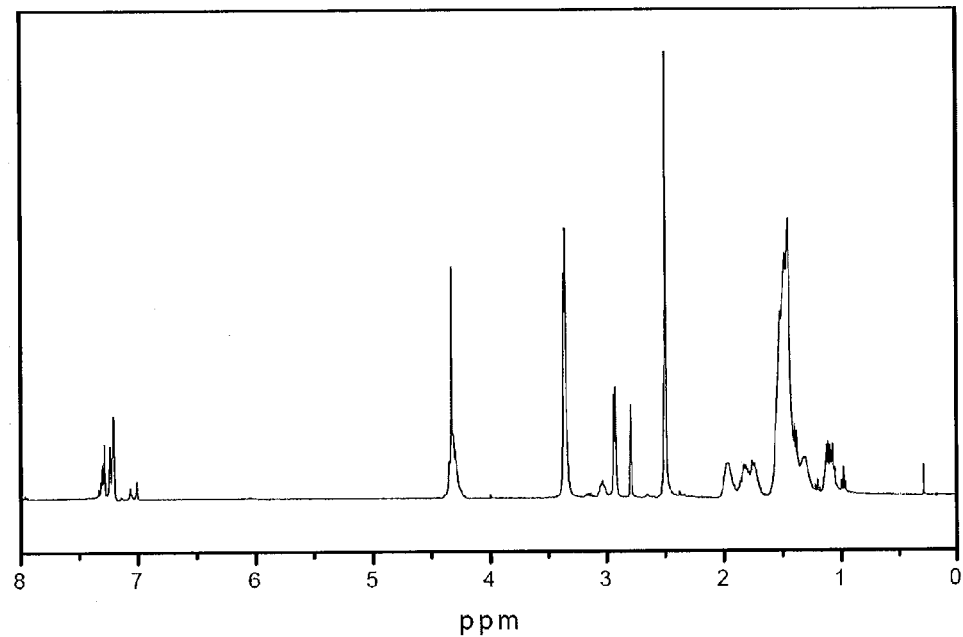
FIG. 7a is the $^1$H-NMR spectrum of the target product in example 2.
Figure 7B:
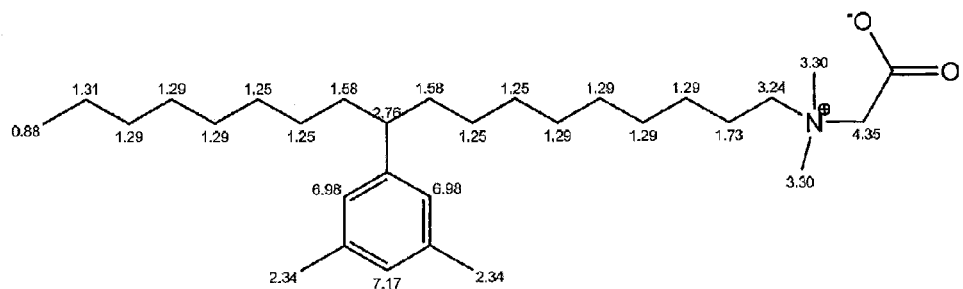

(5) The reaction product of step (4) xylene α octadecyl tertiary amine is reacted with sodium chloroacetate in methanol solvent at 130° C. and 0.3 MPa, yielding target betaine surfactant. The spectra confirming the structure are shown in FIGS. 7a and 7b.

INDUSTRIAL APPLICABILITY

Example (1) Ultralow Interfacial Tension Testing of Binary System

Figure 8:
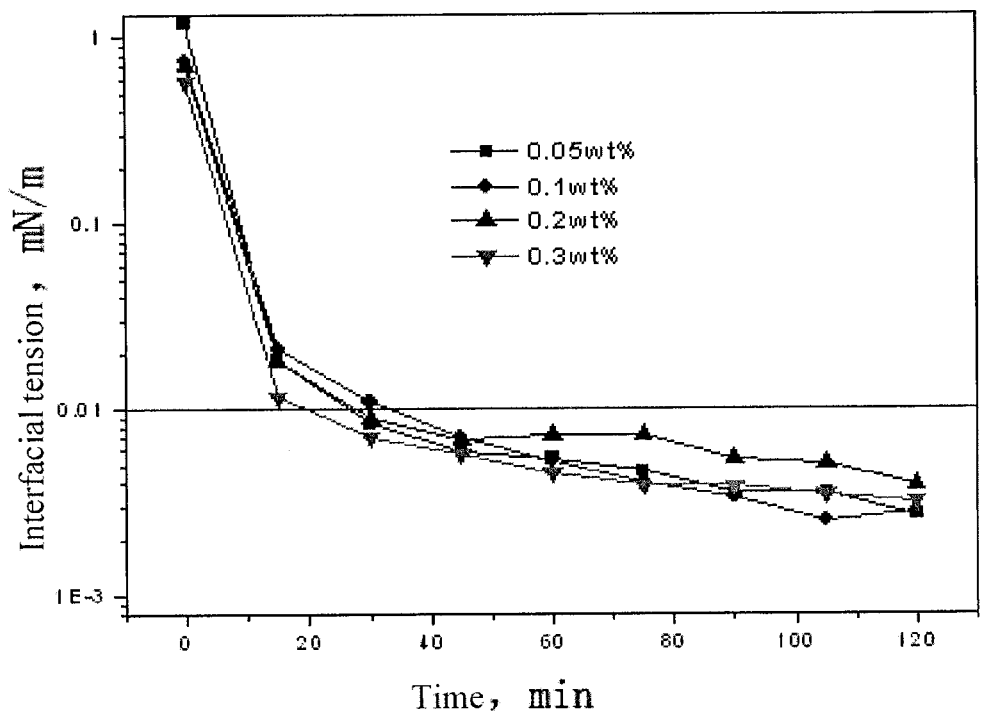
FIG. 8 is the surface tension of binary system, wherein the polymer is hydrophobic polyacrylamide P19000000, 2000 ppm.

For the target product of example 2, the oil/water interfacial activity in the 6$^{th}$ oil production plant of Daqing oilfield conditions is shown in FIG. 8. For binary system, the interfacial tension reaches ultralow level ($10^{-3}$ mN/m or lower magnitude) at a surfactant concentration in a range of 0.05 wt %-0.3 wt %, indicating the excellent performance of the sample in kilogram scale of the synthesized new betaine surfactant.

(2) Ultralow Interfacial Tension Testing of Unitary System

Figure 9:
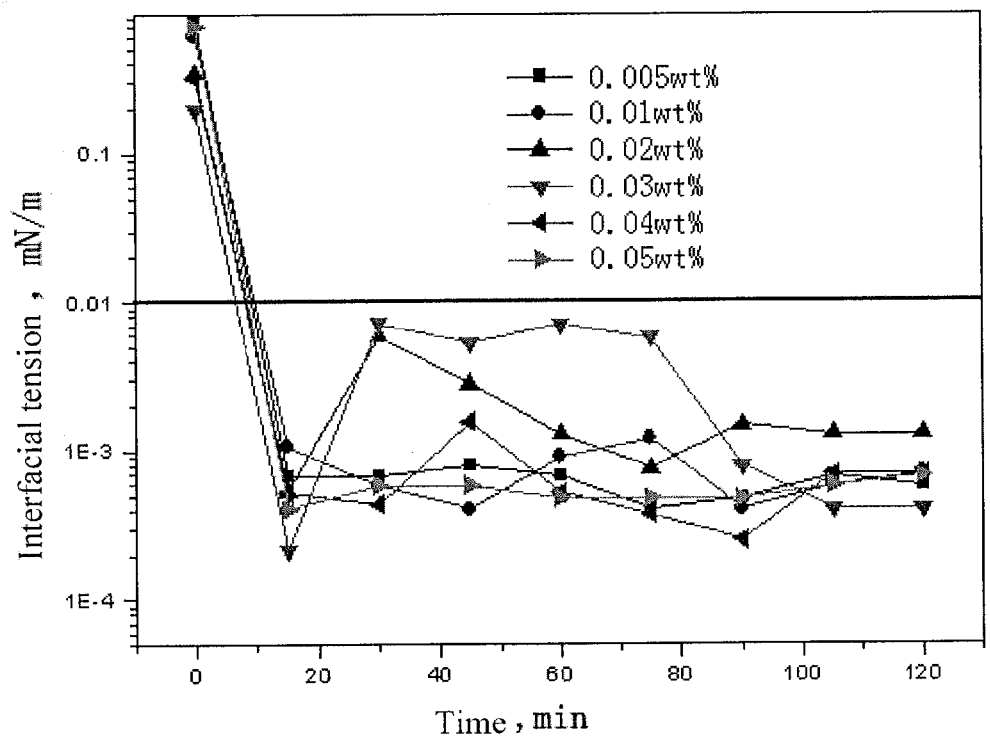
FIG. 9 is the surface tension at low concentration of unitary system.

New aryl alkyl betaine surfactants have excellent capability and efficiency of reducing interfacial tension, and in particular, they show good interfacial activities at rather low concentration. For the unitary system of the surfactant of example 1 at a concentration of 50-500 ppm, the oil/water interfacial tension in the 3$^{th}$ oil production plant of Daqing oilfield conditions is shown in FIG. 9. It can be seen that the interfacial tension reaches ultralow and the interfacial performance are excellent within surfactant concentration range of 50-500 ppm.

(3) Effect of Temperature on Interfacial Activity

Figure 10:
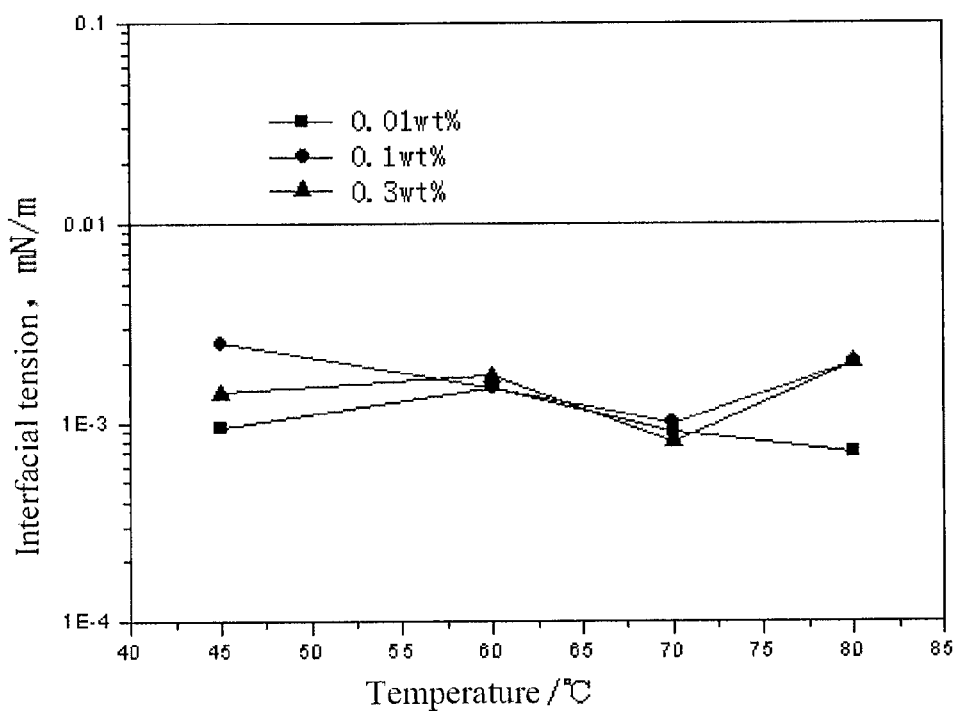
FIG. 10 shows the effect of temperature on interfacial tension.

The crude oil and the recycled produced water of the 4$^{th}$ oil production plant of Daqing oilfield are used and the testing temperature is changed. It is found that for the surfactant of example 1, the fluctuation of interfacial tension is little as the temperature changes, as shown in FIG. 10.

(4) Effect of Salinity and Divalent Ions on Interfacial Tension

One prominent feature of amphoteric surfactants is the high tolerance to brine and divalent ions. Therefore, the tolerance to divalent ions and the adaptability for salinity of the betaine surfactants of examples 1 and 2 are investigated.

Figure 11:
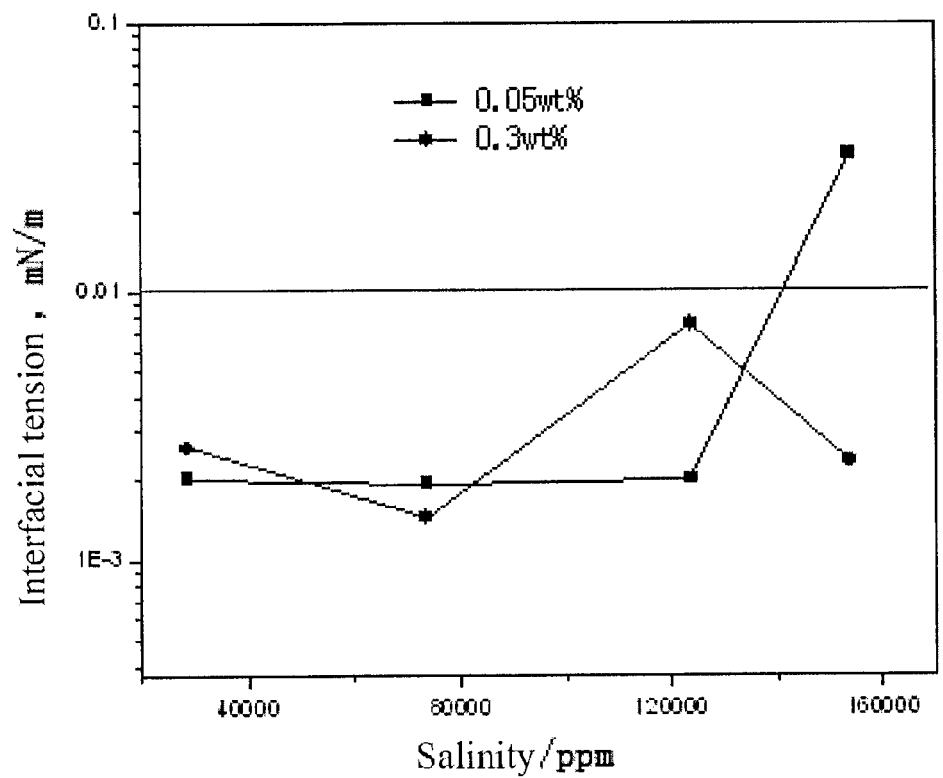
FIG. 11 shows the effect of salinity on interfacial tension.

The effect of salinity on interfacial tension is shown in FIG. 11. It can be seen from FIG. 11 that the betaine surfactant of example 1 shows a tolerance to salinity of up to 150000 mg/L, and is applicable to the formation water of most of the oilfields.

Figure 12:
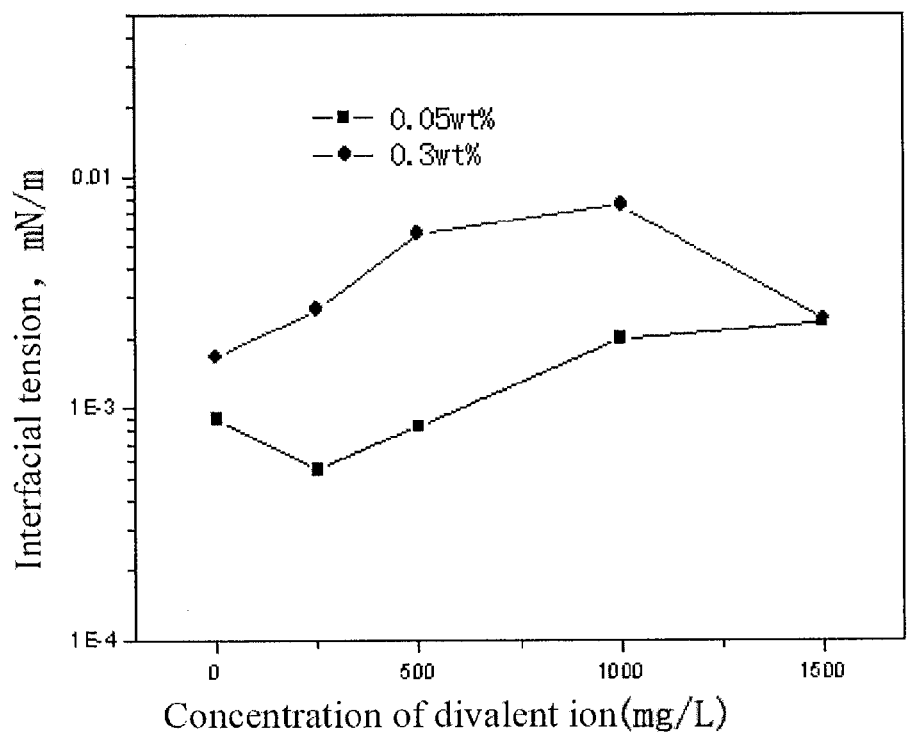
FIG. 12 shows the effect of divalent ion on interfacial tension.

The effect of the divalent ions on the interfacial tension of the betaine surfactant of example 2 is investigated by adding calcium chloride into the formation water in Daqing, as shown in FIG. 12. It can be seen from FIG. 12 that the interfacial tension can still reach ultralow when the concentration of divalent ions reaches 1,500 mg/L.

Figure 13:
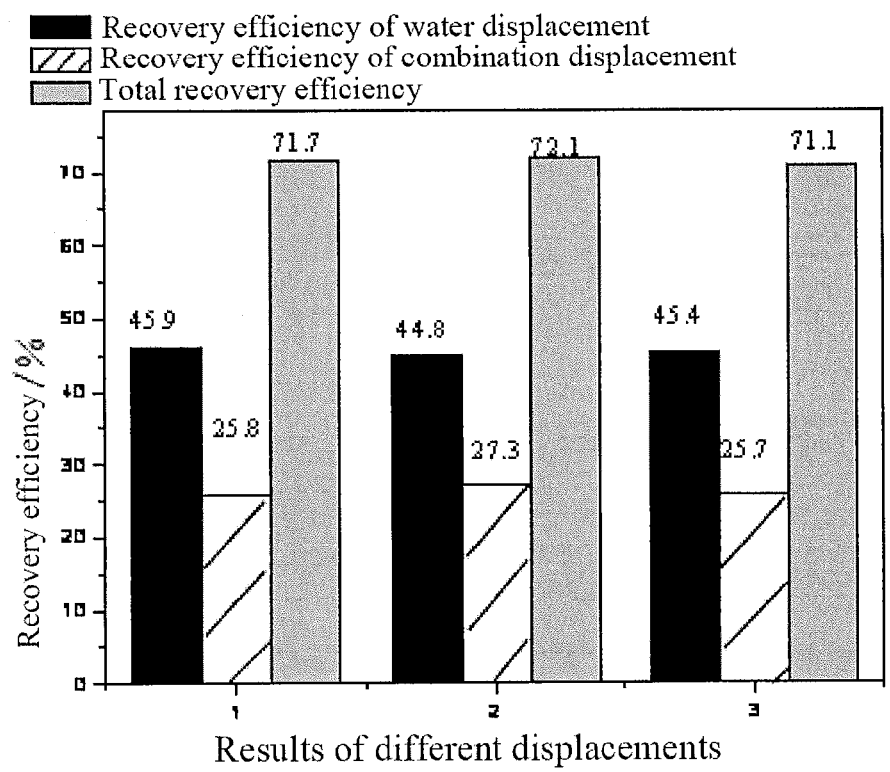
FIG. 13 shows the results of artificial homogenous core displacement for different systems of the surfactants of the present invention.

(5) The Oil-Displacing Experiment Comparison of Artificial Homogenous Core Displacement for Different Oil-Displacing Systems Alkali-free binary system, binary system comprising $Na_2CO_3$ and $Na_3PO_4$ as sacrificial agents and ASP system comprising NaOH show good oil displacing efficiency. The oil displacing efficiencies of the oil displacing approaches as mentioned above are tested on homogeneous core, and the results are shown in FIG. 13, wherein Approach 1 is synthetic sulfo-betaine surfactant 0.2%+polymer 2500 mg/l, 0.35 PV; Approach 2 is synthetic sulfo-betaine surfactant 0.2%+polymer 2500 mg/l+$Na_3PO_4$ 0.4%, 0.35 PV; Approach 3 is synthetic sulfo-betaine surfactant 0.3%+polymer 2500 mg/l+NaOH 1%, 0.35 PV. It should be noted that the protective plug in each approach is P 1000 mg/l 0.20 PV.

The increase in recovery efficiency of alkali-free binary system is comparable to that of the ASP system comprising NaOH, and the recovery efficiency of binary system combination flooding comprising $Na_3PO_4$ as the sacrificial agent is slightly higher than those of the former two approaches.

The present invention produces aryl alkyl betaines from cheap starting materials in market (oleic acid and alkylbenzene) successively subjected to esterification, Friedel-Crafts alkylation, hydrogenation reduction, amination and quaternization. The products of the present invention have five advantages: 1) the reactions are well-developed and the conversion rate is high; 2) the starting materials are cheap and readily available; 3) the aryl groups are present in the middle of the carbon chain; 4) the products have high activities and are able to reduce the interfacial tension for crude oil of No. 1-6 oil production plants of Daqing oilfield to $10^{-3}$ mN/m magnitude without the addition of alkali; 5) the products have high tolerance to temperature (130° C.), salinity and dilution, and are very promising for application in the field of tertiary oil recovery.

The invention claimed is:

1. A betaine surfactant of formula (I):

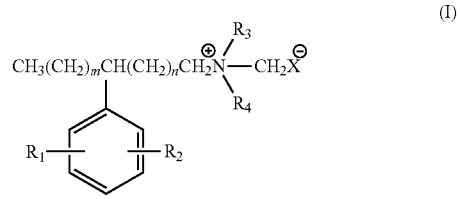

wherein m and n are integers of 2-10, $R_1$ is H or alkyl, $R_2$, $R_3$ and $R_4$ are independently alkyl, and X is selected from the group consisting of

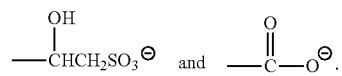

2. The betaine surfactant of claim 1, wherein m+n=5-19.

3. The betaine surfactant of claim 2, wherein m+n is an integer of 9-17.

4. The betaine surfactant of claim 3, wherein m and n are positive integers of 7 or 8, and m+n=15.

5. The betaine surfactant of claim 1, wherein $R_1$ is H or C1-C8 alkyl, $R_2$ is C1-C8 alkyl, and $R_3$ and $R_4$ are independently C1-C4 alkyl.

6. The betaine surfactant of claim 1, wherein $R_1$ is H or C1-C4 alkyl, $R_2$ is C1-C4 alkyl, and $R_3$ and $R_4$ are independently C1-C2 alkyl.

7. The betaine surfactant of claim 1, wherein $R_1$ is H or C1-C2 alkyl, and $R_2$ is C1-C2 alkyl.

8. The betaine surfactant of claim 1, wherein the para position of —$CH(CH_3(CH_2)_m(CH_2)_n CH_2NR_3R_4CH_2X$ is H.

9. The betaine surfactant of claim 8, wherein $R_1$ and $R_2$ are at meta positions of —$CH(CH_3(CH_2)_m(CH_2)_n CH_2NR_3R_4CH_2X$, and both $R_1$ and $R_2$ are methyl.

10. The betaine surfactant of claim 8, wherein $R_1$ is H, and $R_2$ is methyl.

11. The betaine surfactant of claim 8, wherein $R_1$ is H, and $R_2$ is ethyl.

\* \* \* \* \*